United States Patent [19]

Iwasaki

[11] Patent Number: 4,681,900

[45] Date of Patent: Jul. 21, 1987

[54] BIOCIDE ACTIVATOR

[75] Inventor: Tetsuji Iwasaki, Wakayama, Japan

[73] Assignee: Kao Corporation, Tokyo, Japan

[21] Appl. No.: 689,904

[22] Filed: Jan. 9, 1985

[30] Foreign Application Priority Data

Jan. 13, 1984 [JP] Japan .................................... 59-4569

[51] Int. Cl.$^4$ ..................... A01N 25/00; A01N 25/02; C11C 3/00
[52] U.S. Cl. ............................... 514/786; 71/DIG. 1; 260/410.6; 260/410.7; 514/567; 514/785
[58] Field of Search ....................... 514/567, 785, 786; 260/410.6, 410.7; 71/DIG. 1

[56] References Cited

U.S. PATENT DOCUMENTS

| | | | |
|---|---|---|---|
| 2,678,935 | 5/1954 | Sundberg et al. | 260/410.6 |
| 2,786,013 | 3/1957 | Behrens | 514/785 |
| 2,819,996 | 1/1958 | Riley | 514/785 |
| 2,975,099 | 3/1961 | Goyan et al. | 514/785 |
| 3,095,353 | 6/1963 | Surgant | 514/785 |
| 3,192,193 | 6/1965 | Altscher et al. | 260/410.6 |
| 3,312,542 | 4/1967 | Kitzke et al. | 260/410.7 |
| 3,776,857 | 12/1973 | Lindner | 514/785 |
| 3,910,972 | 10/1975 | Dieckelmann et al. | 260/410.6 |
| 4,035,514 | 7/1977 | Davis | 514/786 |
| 4,195,075 | 3/1980 | Miller | 424/14 |

FOREIGN PATENT DOCUMENTS

| | | | |
|---|---|---|---|
| 1066047 | 9/1959 | Fed. Rep. of Germany | 514/785 |
| 34815 | 9/1974 | Japan | 514/785 |
| 95107 | 8/1981 | Japan | 514/785 |

*Primary Examiner*—J. E. Evans
*Attorney, Agent, or Firm*—Flynn, Thiel, Boutell & Tanis

[57] ABSTRACT

A biocide activator is disclosed which is a product prepared by adding propylene oxide, alone or together with ethylene oxide, to a mixture of a fatty acid triglyceride and a polyhydric alcohol under conditions effective to cause addition polymerization. This activator exhibits a remarkable biocide enhancing-effect without harm to various crops when used with existing biocides such as insecticides, fungicides, herbicides and plant growth regulators.

17 Claims, No Drawings

BIOCIDE ACTIVATOR

This invention relates to a biocide activator. In this description, the term "biocide" shall mean a material that destroys or inhibits unwanted organisms, such as plants, animals and bacteria.

Biocides, including insecticides, fungicides, herbicides and plant growth regulators, have been used in various forms such as emulsions, wettable powders, flowable agents, granules and dusts. In formulating these biocides numerous attempts have been made to utilize the activity of the active principle thereof sufficiently. However, no activator for such biocides has been disclosed as yet.

As it has become more and more difficult to develop new biocides, it will be highly advantageous if known biocides can be activated by means of an additive activating substance which enhances the activity of the biocide.

We have discovered that particular compounds exhibit an activating effect on various biocides. The present invention provides a biocide activator comprising a product which is prepared by reacting (1) propylene oxide, alone or together with ethylene oxide, with (2) a mixture of at least one fatty acid triglyceride and at least one polyhydric alcohol, under conditions effective to cause addition polymerization of the propylene oxide or propylene oxide and ethylene oxide, with the fatty acid triglyceride and polyhydric alcohol. The present invention further provides a biocidal composition which comprises an effective amount of a biocide such as an insecticide, bactericide, miticide, fungicide, herbicide or plant growth regulator, an effective amount of the foregoing biocide activator, and a carrier. The present invention further provides a dilute biocidal composition formed by diluting the foregoing biocidal composition with water, so that the concentration of the biocide is at least 25 parts per million and the concentration of the activator is at least 50 parts per million. As a preferred form of biocidal composition according to the invention, a biocidal emulsion concentrate is disclosed which contains 10-70 weight percent of the biocide, 10-50 weight percent of the activator, 3-20 weight percent of the emulsifier, and 10-50 weight percent of an organic solvent. In a preferred embodiment, the biocidal emulsion concentrate contains 20-55 weight percent of the biocide, 20-30 weight percent of the activator, 5-10 weight percent of the emulsifier, and 15-45 weight percent of the organic solvent.

The fatty acid triglyceride used in preparing the biocide activator of the present invention is not particularly limited, and triglycerides of higher fatty acids ($C_4$-$C_{22}$) such as behenic, stearic, oleic, linoleic, palmitic, myristic, lauric and caprylic acid are preferably used. These higher fatty acids can be employed individually, or mixtures of at least two of them can be employed. The fatty acid triglyceride can be either a natural material or a synthetic product. Natural fats and oils which are natural fatty acid triglycerides are readily available and suitable for use in the present invention. Examples of these natural fats and oils are animal fats and oils such as beef tallow, lard, bone oil and mutton tallow, vegetable fats and oils such as coconut oil, palm oil, cottonseed oil, castor oil, rapeseed oil, coconut kernel oil, soybean oil, olive oil, linseed oil and corn oil, and various fish oils.

The polyhydric alcohol used in the present invention is preferably one having 2 to 6 carbon atoms and 2 to 6 hydroxyl groups, wherein the number of the hydroxyl groups does not exceed the number of carbon atoms. Example of these polyhydric alcohols are ethylene glycol, propylene glycol, glycerol, 1,2-, 1,3- and 2,3-butylene glycols, 1,2-, 1,3-, 2,3- and 2,4-pentylene glycols, 1,2-, 1,3-, 2,3- and 2,4-hexylene glycols, butanetriol, pentanetriol, hexanetriol, pentaerythritol, sorbitol, sorbitan, mannitol, xylitol, and dulcitol.

Among these polyhydric alcohols, it is preferable to employ polyhydric alcohols having three carbon atoms, pentaerythritol, or sorbitol. Glycerol is most preferred for achieving the objects of the present invention. A mixture of these polyhydric alcohols may be employed.

The molar ratio of fatty acid triglyceride(s):polyhydric alcohol(s) is from 1:0.1 to B 1:5, preferably from 1:0.2 to 1:2.

The alkylene oxide to be added to the mixture of fatty acid triglyceride(s) and polyhydric alcohol(s) is critical in the present invention. This alkylene oxide added to said mixture in the present invention consists of propylene oxide, or consists of both propylene oxide and ethylene oxide. The propylene oxide is preferably added to said mixture in an amount of 1 to 100 mol, most preferably 3 to 50 mol, per 1 mol of the sum of the mols of the fatty acid triglyceride(s) and the mols of the polyhydric alcohol(s).

When both propylene oxide and ethylene oxide are used they can be added to said mixture in any order. Either block addition or random addition can be employed. The ethylene oxide is preferably added in an amount of 1 to 100 mol, most preferably 5 to 60 mol, per 1 mol of the sum of the mols of the fatty acid triglyceride(s) and the mols of the polyhydric alcohol(s).

The addition can be carried out under conventional conditions generally employed for adding an alkylene oxide to a compound having active hydrogen without particular limitation. Thus, the addition reaction can be carried out by adding an alkaline compound such as NaOH, KOH, sodium acetate, $CH_3ONa$ and $CH_3OK$, as a catalyst, to a mixture of triglyceride(s) and polyhydric alcohol(s) in the above mentioned molar ratios and feeding an alkylene oxide thereto, at a temperature of approximately 100° C. to 200° C. and a pressure of 1 to 5 kg/cm² gauge over a period of at least about an hour, usually several hours, to thereby allow the materials to react with each other.

The product formed by the above reaction is a mixture of various polymers and the details of its composition are presently unknown. However, it is assumed that the main component thereof is a material in which propylene oxide, alone or together with ethylene oxide, is inserted between (1) the fatty acid constituting part of the original fatty acid triglyceride and (2) a polyhydric alcohol or (3) glycerol originating from the fatty acid triglyceride. Such compounds would contain a linkage of which an example is:

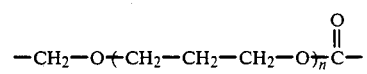

wherein n is the number of repeating units derived from the added propylene oxide.

The biocide activator of the present invention is not harmful when it is used with a biocide and it generally enhances the activity of the biocide by two to three times, regardless of the type of biocide with which it is employed. The activator of the present invention is advantageously used in an amount of 0.1 to 5 parts by weight, preferably 0.5 to 3 parts by weight, per 1 part by weight of the active biocide principle.

A biocide composition containing the activator of the present invention can be formulated into a concentrated form such as a flowable agent, a wettable powder or a dust. Conventional additives such as an emulsifier, dispersant or carrier can be added, depending on the formulation. An emulsifier may be chosen so as to provide the resultant with a good emulsion state. These concentrates are generally diluted with water, before use. The activator of the present invention can be added to the biocide during the formulation of one of the abovementioned biocide compositions or during dilution thereof at the time of use. The activator exhibits activating effects as defined in the present invention in either case.

In the biocidal emulsion concentrate according to the invention, the organic solvent is preferably an aromatic hydrocarbon, most preferably xylene. The emulsifier contained in the biocidal emulsion concentrate preferably contains alkylbenzene sulfonate and at least two different polyoxyethylene compounds from among polyoxyethylene nonylphenol ether, polyoxyethylene oleyl ester, polyoxyethylene styrenated phenol ether and polyoxyethylene tribenzylphenol ether. The emulsifier according to the invention preferably consists of 20-40 weight percent of alkylbenzenesulfonate and 60-80 weight percent of one or more of the foregoing polyoxyethylene compounds.

The mechanism of the remarkable activating effect of the biocide activator of the present invention has not yet been determined. This activating effect might partly be due to the extremely high solubilizing effect of the activator of the present invention on a biocide which would break up the biocide into microparticles to thereby accelerate the penetration thereof through the surfaces of plants or into the bodies of insects or bacteria. In view of this fact, it is preferred to use the biocide activator of the present invention in a concentration of at least 50 ppm when diluted in an aqueous biocide composition.

Accordingly, the present invention further provides a process for controlling organisms which comprises spraying a dilute biocide composition, particularly an emulsion or dispersion, containing at least 50 ppm of a composition prepared by adding propylene oxide, alone or together with ethylene oxide, to a mixture of fatty acid triglyceride(s) and polyhydric alcohol(s) under conditions effective to cause addition polymerization.

Non-limiting examples of the biocides to which the activator of the present invention can be added are as follows. The products of the present invention can be safely applied on a wide variety of crops without harm. Thus, the activator of the present invention can be used with insecticides including pyrethroid insecticides such as Fenvalerate (-cyano-3-phenoxybenzyl 2-(4-chlorophenyl)-3-methylvalerate) and Baisroid (cyano-(4-fluoro-3-phenoxyphenylmethyl)-3-(2,2-dichloroethenyl)-2,2-dimethylcyclopropanecarboxylate), organophosphorus insecticides such as DDVP (2,2-dichlorovinyl dimethyl phosphate), Sumithion (dimethyl 4-nitro-m-tolyl phosphorothionate), Malathion (S-[1,2-bis(ethoxycarbonyl)ethyl]dimethyl phosphorothiolothionate), Dimethoate (dimethyl-S-(N-methylcarbamoylmethyl)-phosphorothiolothionate, Elsan (S-[α-(ethoxycarbonyl)benzyl]dimethyl phosphorothiolothionate, and Baycide (O,O-dimethyl-O-(3-methyl-4-methylmercaptophenyl)thiophosphate), carbamate insecticides such as Bassa (o-butylphenyl methylcarbonate), MTMC (m-tolyl methylcarbamate), Meobal (3,4-dimethylphenyl-N-methylcarbamate) and NAC (1-naphthyl N-methylcarbamate), and bactericides such as Methomyl (methyl-N-((methylcarbamoyl)oxy)thioacetoimide) and Cartap (1,3-bis(carbamoylthio)-2-(N,N-dimethylamino) propane hydrochloride.

The activator of the present invention can also be used with miticides such as Smite (2-(2-p-tert-butylphenoxy)isopropoxy)isopropyl-2-chloroethyl sulfide), Acricid (2,4-dinitro-6-sec-butylphenyl dimethylacrylate), Chlormite (isopropyl 4,4-dichlorobenzilate), Akar (ethyl 4,4-dichlorobenzilate), Kelthane (1,1-bis(p-chlorophenyl)-2,2,2-trichloroethanol), Citrazon (ethyl O-benzoyl-3-chloro-2,6-dimethoxybenzohydroxamate), Plictran (tricyclohexyltin hydroxide) and Omite (2-(p-tert-butylphenoxy)-cyclohexyl 2-propynyl sulfite).

The activator of the invention, can further be used with fungicides including organosulfur fungicides such as Dithane (zinc ethylenebisdithiocarbamate), Maneb (manganese ethylenebisdithiocarbamate), Thiram (bis-(dimethylthiocarbamoyl)disulfide), and other fungicides such as Benlate (methyl 1-(butylcarbamoyl)-2-benzimidazolecarbamate), Difolatan (N-(tetrachloroethylthio)-4-cyclohexene-1,2-dicarboxyimide), Daconol (tetrachloroisophthalonitrile), Pansoil (5-ethoxy-3-trichloromethyl-1,2,4-thiadiazole), Thiophanate-Methyl (1,2-bis(3-methoxycarbonyl-2-thioureido)benzene), Rabcide (4,5,6,7-tetrachlorophthaloid), Kitazin P (O,O-diisopropyl S-benzyl phosphorothioate), Hinosan (O-ethyl S,S-diphenyl dithiophosphate and Propenasol (3-allyloxy-1,2-benzothiazole-1,1-dioxide).

The activator of the invention can be used with herbicides such as Stam (3,4-dichloropropionanilide), Saturn (S-(4-chlorobenzyl)-N,N-diethylthiolcarbamate), Lasso (2-chloro-2',6'-diethyl-N-(methoxymethyl)-acentanilide), Glyphosate (N-(phosphonomethyl)glycine isopropylamine salt), DCMU (3-(3,4-dichlorophenyl)-1,1-dimethylurea) and Gramoxone (1,1-dimethyl-4,4'-dipyridium dichloride), and with plant growth regulators such as MH (maleic hydrazide) and Ethrel (2-chlor ethyl phosphate).

To illustrate biocide compositions containing the biocide activator of the present invention, the following examples each showing the formulation of concentrated biocide compositions will be given. Unless otherwise state, quantities are expressed in percent by weight.

| Example 1 | |
|---|---|
| Sumithion | 55% |
| xylene | 15 |
| polyoxypropylene (5) polyoxyethylene (40) olive oil/glycerol (0.5/0.5) ester | 20 |
| Emulsifier 1 | 10 |
| Comparative Example 1 | |
| Sumithion | 55% |
| xylene | 35% |
| Emulsifier 2 | 10 |
| Example 2 | |
| Fenvalerate | 20% |
| xylene | 44 |
| polyoxypropylene (20) polyoxyethylene (60) bone oil/glycerol (0.5/0.5) ester | 30 |
| Emulsifier 3 | 6 |
| Comparative Example 2 | |
| Fenvalerate | 20% |
| xylene | 74 |
| Emulsifier 4 | 6 |

-continued

| Example 3 | |
|---|---|
| Bassa | 55% |
| xylene | 15 |
| polyoxyethylene (10) polyoxypropylene (20) rapeseed oil/sorbitol (0.5/0.5) ester | 20 |
| Emulsifier 5 | 10 |
| Comparative Example 3 | |
| Bassa | 55% |
| xylene | 15 |
| polyoxyethylene (20) rapeseed oil/sorbitol (0.5/0.5) ester | 20 |
| Emulsifier 6 | 10 |
| Example 4 | |
| Omite | 40% |
| xylene | 30 |
| polyoxypropylene (10) beef tallow/sorbitol (0.5/0.5) ester | 20 |
| Emulsifier 7 | 10 |
| Comparative Example 4 | |
| Omite | 40% |
| xylene | 30 |
| polyoxyethylene (10) beef tallow/sorbitol (0.5/0.5) ester | 20 |
| Emulsifier 8 | 10 |
| Example 5 | |
| Kelthane | 40% |
| xylene | 30 |
| polyoxyethylene (35) polyoxypropylene (5) fish oil/pentaerythritol (0.5/0.5) ester | 20 |
| Emulsifier 9 | 10 |
| Comparative Example 5 | |
| Kelthane | 40% |
| xylene | 50 |
| Emulsifier 10 | 10 |
| Example 6 | |
| Hinosan | 55% |
| xylene | 15 |
| polyoxypropylene (30) lard/glycerol (0.5/0.5) ester | 20 |
| Emulsifier 11 | 10 |
| Comparative Example 6 | |
| Hinosan | 55% |
| xylene | 35 |
| Emulsifier 12 | 10 |
| Example 7 | |
| Daconol | 50% |
| polyoxyethylene (30) polyoxypropylene (10) coconut oil/glucose (0.5/0.5) ester | 20 |
| clay | 26 |
| Dispersant 1 | 4 |
| Comparative Example 7 | |
| Daconol | 50% |
| clay | 46 |
| Dispersant 1 | 4 |
| Example 8 | |
| Saturn | 55% |
| polyoxyethylene (10) polyoxypropylene (10) coconut oil/glycerol (0.5/0.5) ester | 20 |
| xylene | 15 |
| Emulsifier 13 | 10 |
| Comparative Example 8 | |
| Saturn | 55% |
| xylene | 40 |
| Emulsifier 14 | 5 |
| Example 9 | |
| potassium maleic hydrazide | 22% |
| polyoxypropylene (40) polyoxyethylene (20) olive oil/glycerol (0.5/0.5) ester | 25 |
| water | 53 |
| Comparative Example 9 | |
| potassium maleic hydrazide | 22% |
| polyoxyethylene nonylphenol ether | 25 |
| water | 53 |

The compositions of the Emulsifiers 1 to 14 and the Dispersant 1 used in the above examples were as follows

| Emulsifier 1 | |
|---|---|
| alkylbenzenesulfonate | 32% |
| polyoxyethylene (11) nonylphenol ether | 16 |
| polyoxyethylene (20) styrenated phenol ether | 52 |
| Emulsifier 2 | |
| alkylbenzenesulfonate | 32% |
| polyoxyethylene (11) nonylphenol ether | 28 |
| polyoxyethylene (20) styrenated phenol ether | 40 |
| Emulsifier 3 | |
| alkylbenzenesulfonate | 30% |
| polyoxyethylene (15) nonylphenol ether | 20 |
| polyoxyethylene (20) oleyl ester | 50 |
| Emulsifier 4 | |
| alkylbenzenesulfonate | 30% |
| polyoxyethylene (15) nonylphenol ether | 35 |
| polyoxyethylene (20) oleyl ester | 35 |
| Emulsifier 5 | |
| alkylbenzenesulfonate | 32% |
| polyoxyethylene (10) nonylphenol ether | 20 |
| polyoxyethylene (25) styrenated phenol ether | 48 |
| Emulsifier 6 | |
| alkylbenzenesulfonate | 32% |
| polyoxyethylene (10) nonylphenol ether | 10 |
| polyoxyethylene (25) styrenated phenol ether | 58 |
| Emulsifier 7 | |
| alkylbenzenesulfonate | 30% |
| polyoxyethylene (20) oleyl ester | 30 |
| polyoxyethylene (16) tribenzylphenol ether | 40 |
| Emulsifier 8 | |
| alkylbenzenesulfonate | 30% |
| polyoxyethylene (20) oleyl ester | 45 |
| polyoxyethylene (16) tribenzylphenol ether | 25 |
| Emulsifier 9 | |
| alkylbenzenesulfonate | 25% |
| polyoxyethylene (20) nonylphenol ether | 25 |
| polyoxyethylene (35) styrenated phenol ether | 50 |
| Emulsifier 10 | |
| alkylbenzenesulfonate | 25% |
| polyoxyethylene (20) nonylphenol ether | 40 |
| polyoxyethylene (35) styrenated phenol ether | 35 |
| Emulsifier 11 | |
| alkylbenzenesulfonate | 30% |
| polyoxyethylene (15) styrenated phenol ether | 30 |
| polyoxyethylene (15) oleyl ester | 40 |
| Emulsifier 12 | |
| alkylbenzenesulfonate | 30% |
| polyoxyethylene (15) styrenated phenol ether | 10 |
| polyoxyethylene (15) oleyl ester | 60 |
| Emulsifier 13 | |
| alkylbenzenesulfonate | 30% |
| polyoxyethylene (11) nonylphenol ether | 15 |
| polyoxyethylene (30) styrenated phenol ether | 55 |
| Emulsifier 14 | |
| alklybenzenesulfonate | 30% |
| polyoxyethylene (11) nonylphenol ether | 25 |
| polyoxyethylene (30) styrenated phenol ether | 45 |
| Dispersant 1 | |
| ammonium sulfate salt of naphthalene/ formaldehyde condensate | 50% |
| sodium lauryl sulfate | 50 |

The effects of the activator of the present invention will be described in the following test examples. In these examples, the biocidal concentrates of the examples and comparative examples were diluted with water so that the concentrations of the biocides were as indicated below in parts per million (ppm).

TEST EXAMPLE 1

Ten rice insect larvae of 3rd instar per area were grown triply to examine the effect of the biocide compositions of the examples by a leaf-dipping method wherein insects were allowed to infest each of a number of plant leaves, and the plant leaves infested with the insects were then dipped in the biocide compositions. In the test, the plant leaves having thereon the insects were dipped into the biocide composition solution for about 3 seconds. Then they were taken out and allowed to stand for a while. After a certain period of time had passed, the number of dead insects were calculated and an insecticidal ration was determined. The part of the leaf that was dipped into the biocide composition is referred to as the treated area, and the part thereof that was not dipped is referred to as the non-treated area. The insecticidal ratio was determined by comparing insect density of the treated area with insect density of the non-treated area 24 hours after the treatment. The insecticidal ratio is expressed as the percent reduction in the number of insects in the treated area caused by the biocide composition treatment, as compared to the non-treated area. The other ratios described hereafter in Test Examples 3 to 7 are calculated in the same manner, except that the pests other than insects were treated. The 50% lethal concentration ($LC_{50}$) was also determined. The results are shown in Table 1.

TABLE 1

|  | Concentration of active principle | Biocide EX. 1 | Biocide Comp. EX. 1 | Biocide EX. 3 | Biocide Comp. EX. 3 |
| --- | --- | --- | --- | --- | --- |
| Insecticidal ratio (%) | 100 pm | 88 | 53 | 72 | 50 |
|  | 75 | 80 | 30 | 68 | 40 |
|  | 50 | 65 | 24 | 60 | 26 |
|  | 25 | 40 | 10 | 34 | 8 |
| $LC_{50}$ (ppm) |  | 33 | 97 | 40 | 100 |

TEST EXAMPLE 2

*Memestra brassicae* larvae of 3rd instar per area were grown triply to examine the effect of biocide compositions by the leaf-dipping method described above. The insecticidal ratio was determined by comparison with the non-treated area 24 hours after the treatment. The 50% lethal concentration was also determined. Results are shown in Table 2.

TABLE 2

|  | Concentration of active principle | Biocide EX. 2 | Biocide Comp. EX. 2 |
| --- | --- | --- | --- |
| Insecticidal ratio (%) | 100 ppm | 95 | 58 |
|  | 75 | 84 | 40 |
|  | 50 | 70 | 34 |
|  | 25 | 46 | 12 |
| $LC_{50}$ (ppm) |  | 27 | 83 |

TEST EXAMPLE 3

30 female *Tetranychus urtiae* imagoes per area were inoculated triply and grown at 25° C. for 24 hours to thereafter examine the miticidal effect of biocide compositions by the leaf-dipping method as described above. The miticidal ratio was determined by comparison with the non-treated area 24 hours after the treatment. The 50% lethal concentration was also determined. Results are shown in Table 3.

TABLE 3

|  | Concentration of active principle | Biocide EX. 4 | Biocide Comp. EX. 4 | Biocide EX. 5 | Biocide Comp. EX. 5 |
| --- | --- | --- | --- | --- | --- |
| Miticidal ratio (%) | 500 ppm | 100 | 68 | 98 | 60 |
|  | 250 | 82 | 46 | 80 | 52 |
|  | 125 | 68 | 22 | 78 | 38 |
|  | 62.5 | 45 | 10 | 47 | 16 |
| $LC_{50}$ (ppm) |  | 75 | 325 | 70 | 300 |

TEST EXAMPLE 4

Young rice plants of pentafoliate stage were inoculated with *Pyricularia oryzae* and allowed to stand for 24 hours, whereby the plants became infected with *Pyricularia oryzae*. Then biocide compositions were sprayed thereon and the formed lesions were counted six months after the treatment to calculate the control ratio (%) by comparison with non-treated area of each plant. The control ratio was determined as the percent reduction in the number of lesions in the treated areas as compared to the non-treated areas. The 50% lesion controlling concentration or amount needed to reduce the number of lesions by 50%, was also determined. Results are shown in Table 4.

TABLE 4

|  | Concentration of active principle | Biocide EX. 6 | Biocide Comp. EX. 6 |
| --- | --- | --- | --- |
| Control ratio (%) | 500 ppm | 100 | 75 |
|  | 250 | 88 | 60 |
|  | 125 | 69 | 42 |
|  | 62.5 | 42 | 28 |
| 50% Controlling concentration (ppm) |  | 80 | 180 |

TEST EXAMPLE 5

Young cucumber plants of trifoliate stage were inoculated with *Sphaerotheca fuliginea* and allowed to stand for 24 hours, whereby the plants became infected with *Sphaerotheca filinginea*. Then biocide compositions were sprayed thereon and the formed lesions were counted seven days after the treatment to calculate the control ratio (%) by comparison with the non-treated area of each plant. The 50% lesion controlling concentration was also determined. Results are shown in Table 5.

TABLE 5

|  | Concentration of active principle | Biocide EX. 7 | Biocide Comp. EX. 7 |
| --- | --- | --- | --- |
| Control ratio (%) | 1000 ppm | 100 | 82 |
|  | 500 | 88 | 64 |
|  | 250 | 62 | 41 |
|  | 125 | 50 | 28 |
|  | 62.5 | 28 | 11 |
| 50% Controlling concentration (ppm) |  | 125 | 310 |

TEST EXAMPLE 6

30 crabgrasses of trifoliate stage per pot were treated with biocide compositions of specified concentrations. Seven days after the treatment, the treated plants were weighed on a wet basis to calculate the herbicidal ratio (%) by comparison with the weight of the non-treated plants. The 50% herbicidal concentration was also determined. Results are shown in Table 6.

TABLE 6

|  | Concentration of active principle | Biocide EX. 8 | Biocide Comp. EX. 8 |
| --- | --- | --- | --- |
| Herbicidal ratio (%) | 2000 ppm | 100 | 95 |
|  | 1000 | 92 | 80 |
|  | 500 | 75 | 61 |
|  | 250 | 54 | 38 |
|  | 125 | 41 | 10 |
| 50% Herbicidal concentration (ppm) |  | 210 | 375 |

TEST EXAMPLE 7

One tobacco plant (Virginia) per pot (φ ca. 13.2 cm) was grown and subjected to topping at the time of 50% flowering. Biocide compositions of specified concentrations were then immediately sprayed thereon and the plants were allowed to stand for 14 days. Subsequently auxillary buds from treated plant areas were weighed on a wet basis to calculate the auxillary bud inhibition ratio by comparison with non-treated areas. The 50% auxillary bud inhibitory concentration was also determined. Results are shown in Table 7.

TABLE 7

|  | Concentration of active principle | Biocide EX. 9 | Biocide Comp. EX. 9 |
| --- | --- | --- | --- |
| Auxiliary Bud inhibitory ratio (%) | 600 ppm | 92 | 78 |
|  | 300 | 84 | 52 |
|  | 150 | 60 | 38 |
|  | 75 | 40 | 10 |
| 50% Auxiliary Bud inhibitory concentration (ppm) |  | 110 | 320 |

The foregoing Test Examples 1 to 7 indicate that the biocide activator of the present invention greatly enhances the activity of a wide variety of biocides.

The biocide activator according to the invention comprises a polymeric composition. The polymeric composition is prepared by the process as disclosed before. Embodiments of the process are disclosed below.

PREPARATION EXAMPLE 1

A reaction vessel was charged with 370 g of coconut oil, 52 g of glycerol and 1.6 g of potassium hydroxide and purged with nitrogen gas. When the reaction mixture had been heated up to a temperature of 115° to 125° C., 249 g of propylene oxide was added gradually over a period of 3 hours under a pressure of 1.0 to 3.0 kg/cm²G. Then the mixture was aged for 3 hours and further heated up to 150° C. Subsequently 328 g of ethylene oxide was added thereto at 150° to 160° C. at a pressure of 1.0 to 3.0 kg/cm²G and the mixture was aged for 1 hour. Thereafter the reaction system was allowed to stand at 80° to 90° C. at a reduced pressure of 50 Torr. for 30 minutes. It was then neutralized with 1.7 g of acetic acid. The product was found to be a reaction product between coconut oil and glycerol at a molar ratio of 1 to 1 to which 10 moles of propylene oxide and 10 moles of ethylene oxide had been added, having a formula:

(coconut oil)(glycerol)(PO)$_{10}$(EO)$_{10}$H

PREPARATION EXAMPLE 2

A reaction vessel was charged with 536 g of beef tallow, 110 g of sorbitol and 2.8 g of potassium hydroxide and purged with nitrogen gas. Then propylene oxide was added thereto gradually over a period of 3 hours at 115° to 125° C. at a pressure of 1.0 to 3.0 kg/cm²G and the mixture was aged for 3 hours. The reaction product was thereafter allowed to stand at 80° to 90° C. at a reduced pressure of 50 Torr. for 30 minutes. It was neutralized with 1.8 g of acetic acid. The product was found to have a formula:

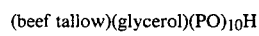

(beef tallow)(glycerol)(PO)$_{10}$H in which beef tallow and glycerol were reacted with each other at a molar ratio of 1 to 1.

The embodiments of the invention in which an exclusive property or privilege is claimed are defined as follows:

1. A composition comprising (A) a carrier, (B) an effective amount of a biocide or plant growth regulator, and (C) from 0.1 to 5 parts by weight, per 1 part by weight of (B), of an activator which is a polymeric composition prepared by a process of adding (1) an alkylene oxide selected from the group consisting of (a) propylene oxide and (b) both of propylene oxide and ethylene oxide, to (2) a mixture of at least one fatty acid triglyceride and at least one polyhydric alcohol, the molar ratio of triglyceride/polyhydric alcohol in said mixture being in the range of from 1/0.2 to 1/2, the addition of said alkylene oxide (1) to said mixture (2) being performed under conditions effective to cause polymerization addition of said alkylene oxide (1) with said mixture (2) to form said polymeric composition, the amount of propylene oxide added to said mixture being in the range of from 1 to 100 mols per 1 mol of the sum of the number of mols of triglyceride and polyhydric alcohol in said mixture.

2. A composition as claimed in claim 1, wherein said polyhydric alcohol is selected from the group consisting of glycerol, pentaerythritol, sorbitol and mixtures thereof.

3. A composition as claimed in claim 1, wherein said fatty acid triglyceride is selected from the group consisting of natural fats, natural oils, and mixtures thereof.

4. A composition as claimed in claim 1 in which the amount of said activator is from 0.5 to 3 parts by weight, per 1 part by weight of (B).

5. A composition comprising (A) a carrier, (B) an effective amount of a biocide or a plant growth regulator, and (C) from 0.1 to 5 parts by weight, per 1 part by weight of (B), of an activator which is a polymeric composition prepared by a process which comprises reacting (1) a mixture of at least one fatty acid triglyceride and at least one polyhydric alcohol having 2 to 6 carbon atoms and 2 to 6 hydroxyl groups, the number of hydroxyl groups not exceeding the number of carbon atoms, wherein the molar ratio of said fatty acid triglyceride to said polyhydric alcohol is in the range of 1:0.2 to 1:2, with (2) an alkylene oxide selected from the group consisting of (a) propylene oxide, wherein the amount of propylene oxide is from 1 to 100 mols per 1 mol of the sum of the number of mols of said fatty acid triglyceride and the number of mols of said polyhydric alcohol in said mixture, and (b) both of propylene oxide, wherein the amount of propylene oxide is from 1 to 100 mols per 1 mol of said molar sum, and ethylene oxide, wherein the amount of ethylene oxide is from 1 to 100 mols per 1 mol of said molar sum, in the presence of an effective amount of a catalyst and under conditions effective to cause addition polymerization of said alkylene oxide (2) with said mixture (1) to form a polymeric composition, and then recovering said polymeric composition.

6. A composition as claimed in claim 5, wherein said polyhydric alcohol is selected from the group consisting of glycerol, pentaerythritol, sorbitol and mixtures thereof, and said fatty acid triglyceride is selected from the group consisting of natural fats, natural oils, and mixtures thereof.

7. A composition as claimed in claim 5, wherein said fatty acid triglyceride is selected from the group consisting of triglycerides of behenic acid, stearic acid, oleic acid, linolic acid, palmitic acid, myristic acid, lauric acid, and caprylic acid, beef tallow, lard, bone oil, mutton tallow, coconut oil, palm oil, cotton seed oil, castor oil, rapeseed oil, coconut kernel oil, soybean oil, olive oil, linseed oil, corn oil, fish oil and mixtures thereof, and said polyhydric alcohol is selected from the group consisting of ethylene glycol, propylene glycol, butylene glycol, pentylene glycol, hexylene glycol, butanetriol, pentanetriol, hexanetriol, pentaerythritol, sorbitol, sorbitan, mannitol, xylitol, dulcitol, and mixtures thereof.

8. A composition as claimed in claim 5, wherein said alkylene oxide (2) is gradually added to said mixture (1) containing said catalyst over a period of at least about 1 hour, and the resulting reaction mixture is maintained at a temperature in the range of 100° C. to 200° C.

9. A composition as claimed in claim 5, wherein said amount of propylene oxide is from 3 to 50 mol per 1 mol of said molar sum, and said amount of ethylene oxide is from 5 to 60 mol per 1 mol of said molar sum.

10. A composition as claimed in claim 5, wherein said biocide is selected from the group consisting of insecticides, bactericides, miticides, fungicides and herbicides.

11. A composition as claimed in claim 10, wherein said activator is selected from the group consisting of polyoxypropylene polyoxyethylene olive oil/glycerol ester, polyoxypropylene polyoxyethylene bone oil/glycerol ester, polyoxypropylene polyoxyethylene rapeseed oil/sorbitol ester, polyoxypropylene beef tallow/sorbitol ester, polyoxypropylene polyoxyethylene fish oil/pentaerythritol ester, polyoxypropylene lard/glycerol ester, polyoxypropylene polyoxyethylene coconut oil/glucose ester, and polyoxypropylene polyoxyethylene coconut oil/glycerol ester.

12. A dilute composition consisting essentially of the composition of claim 10 and an amount of water such that the concentration of said component (B) is at least 25 ppm and the concentration of said activator is at least 50 ppm.

13. A biocide emulsion concentrate consisting essentially of from 10 to 70 wt.% of a biocide, 10 to 50 wt.% of a biocide activator which is a polymeric composition prepared by a process which comprises reacting (1) a mixture of at least one fatty acid triglyceride and at least one polyhydric alcohol having 2 to 6 carbon atoms and 2 to B 6 hydroxyl groups, the number of hydroxyl groups not exceeding the number of carbon atoms, wherein the molar ratio of said fatty acid triglyceride to said polyhydric alcohol is in the range of 1:0.2 to 1:2, with (2) an alkylene oxide selected from the group consisting of (a) propylene oxide, wherein the amount of propylene oxide is from 1 to 100 mols per 1 mol of the sum of the number of mols of said fatty acid triglyceride and the number of mols of said polyhydric alcohol in said mixture, and (b) both of propylene oxide wherein the amount of propylene oxide is from 1 to 100 mols per 1 mol of said molar sum, and ethylene oxide, wherein the amount of ethylene oxide is from 1 to 100 mols per 1 mol of said molar sum, in the presence of an effective amount of a catalyst and under conditions effective to cause addition polymerization of said alkylene oxide (2) with said mixture (1) to form a polymeric composition, and then recovering said polymeric composition, with the proviso that the amount of said biocide activator is from 0.1 to 5 parts by weight, per 1 part by weight of said biocide, 3 to 20 wt.% of an emulsifier and 10 to 50 wt.% of an organic solvent.

14. A biocide emulsion concentrate as claimed in claim 13, consisting essentially of 20 to 55 wt. % of said biocide, 20 to 30 wt. % of said activator, 5 to 10 wt. % of said emulsifier, and 15 to 45 wt. % of said organic solvent.

15. A biocide emulsion concentrate as claimed in claim 14, wherein said organic solvent consists essentially of xylene.

16. A biocide emulsion concentrate as claimed in claim 15, wherein said emulsifier consists essentially of alkylbenzenesulfonate, and at least two polyoxyethylene compounds selected from the group consisting of polyoxyethylene nonylphenol ether, polyoxyethylene oleyl ester, polyoxyethylene styrenated phenol ether, and polyoxyethylene tribenzylphenol ether.

17. A biocide emulsion concentrate as claimed in claim 16, wherein said emulsifier consists of 20 to 40 wt. % of alkylbenzenesulfonate, and 60 to 80 wt. % of said polyoxyethylene compounds.

* * * * *

UNITED STATES PATENT AND TRADEMARK OFFICE
CERTIFICATE OF CORRECTION

PATENT NO. : 4 681 900
DATED : July 21, 1987
INVENTOR(S) : Tetsuji Iwasaki

It is certified that error appears in the above-identified patent and that said Letters Patent is hereby corrected as shown below:

Column 12, line 3; change "2 to B 6" to ---2 to 6---.

Signed and Sealed this

Ninth Day of February, 1988

Attest:

DONALD J. QUIGG

*Attesting Officer*     *Commissioner of Patents and Trademarks*